(12) United States Patent
Andou et al.

(10) Patent No.: US 7,811,793 B2
(45) Date of Patent: Oct. 12, 2010

(54) PROCESS FOR PREPARING PURIFIED ACTIVE MONOMER OF BONE-DERIVED FACTOR

(75) Inventors: Hidetoshi Andou, Miyagi (JP); Jun Honda, Tokyo (JP); Shunjiro Sugimoto, Saitama (JP); Gertrud Hötten, Herne (DE); Rolf Bechtold, Heidelberg (DE); Jens Pohl, Hambrücken (DE)

(73) Assignee: Biopharma Gesellschaft zur Biotechnologischen Entwicklung von Pharmaka MBH, Heidelberg (DE)

( * ) Notice: Subject to any disclaimer, the term of this patent is extended or adjusted under 35 U.S.C. 154(b) by 504 days.

(21) Appl. No.: 10/734,583

(22) Filed: Dec. 15, 2003

(65) Prior Publication Data

US 2005/0026247 A1    Feb. 3, 2005

Related U.S. Application Data

(63) Continuation-in-part of application No. 10/414,954, filed on Apr. 16, 2003, now abandoned, which is a continuation-in-part of application No. 09/331,948, filed as application No. PCT/JP97/04784 on Dec. 24, 1997, now Pat. No. 6,551,801, said application No. 10/414,954 is a continuation-in-part of application No. 10/048,458, filed as application No. PCT/EP00/07600 on Aug. 4, 2000, now Pat. No. 6,972,231, said application No. 10/414,954 is a continuation-in-part of application No. 09/701,121, filed as application No. PCT/IB99/00866 on May 14, 1999, now abandoned.

(30) Foreign Application Priority Data

Dec. 25, 1996  (JP)  .................................. 8-355812
May 22, 1998  (JP)  ................................ 10-141379
Aug. 6, 1999  (EP)  ................................ 99115613

(51) Int. Cl.
*C12P 21/04*   (2006.01)
*C12P 21/06*   (2006.01)
*C12N 1/20*    (2006.01)
*C07K 14/51*   (2006.01)

(52) U.S. Cl. ..................... 435/71.2; 530/412; 435/69.1; 435/252.33

(58) Field of Classification Search ....................... None
See application file for complete search history.

(56) References Cited

U.S. PATENT DOCUMENTS

| | | | |
|---|---|---|---|
| 5,399,677 A | | 3/1995 | Wolfman et al. |
| 5,807,713 A | | 9/1998 | Hötten et al. |
| 5,840,518 A | * | 11/1998 | Morishita et al. .......... 435/69.1 |
| 6,120,760 A | | 9/2000 | Hötten et al. |
| 6,162,257 A | | 12/2000 | Gustilo et al. |
| 6,171,584 B1 | | 1/2001 | Hötten et al. |
| 6,197,550 B1 | | 3/2001 | Hötten et al. |
| 6,531,450 B2 | | 3/2003 | Hötten et al. |
| 6,551,801 B1 | | 4/2003 | Andou et al. |
| 6,972,321 B1 | * | 12/2005 | Hotten et al. ............... 530/350 |

FOREIGN PATENT DOCUMENTS

| | | | |
|---|---|---|---|
| EP | 0433225 | | 6/1991 |
| EP | 1074620 A1 | * | 2/2001 |
| WO | WO 97/04095 | | 2/1997 |
| WO | WO 98/29559 | * | 7/1998 |
| WO | WO 99/66060 | | 12/1999 |
| WO | WO 00/21998 | | 4/2000 |

* cited by examiner

*Primary Examiner*—Marianne P Allen
(74) *Attorney, Agent, or Firm*—Rothwell, Figg, Ernst & Manbeck, P.C.

(57) ABSTRACT

A process for preparing a purified refolded monomer or dimer of a bone-derived factor, which comprises subjecting an inclusion body of a bone-derived factor produced by genetic engineering to the following steps a) to c) in sequence:

Figure 1:
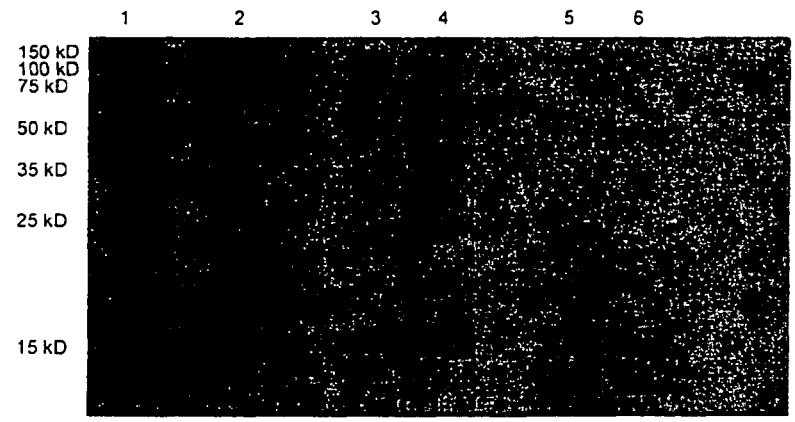

a) introducing a polynucleotide encoding a bone morphogenetic factor into a bacterium, expressing said bone morphogenetic factor in the form of an inclusion body, recovering said inclusion body and treating it with a denaturing agent to obtain a solubilized monomer, b) treating the solubilized monomer without purification directly with a refolding solution to obtain a refolded monomeric bone morphogenetic factor, c) subjecting the refolded monomeric bone morphogenetic factor to purification.

3 Claims, 4 Drawing Sheets

SEQUENCE LISTING

```
<160> NUMBER OF SEQ ID NOS: 1

<210> SEQ ID NO 1
<211> LENGTH: 119
<212> TYPE: PRT
<213> ORGANISM: Homo sapiens
<220> FEATURE:
<221> NAME/KEY: MISC_FEATURE
<222> LOCATION: (83)..(83)
<223> OTHER INFORMATION: Xaa = cysteine for producing active dimeric
      MP52; Xaa = any amino acid preferably except cysteine, and
      especially preferably alanine, serine, threonine, leucine,
      isoleucine, glycine or valine for producing active monomeric MP52

<400> SEQUENCE: 1

Pro Leu Ala Thr Arg Gln Gly Lys Arg Pro Ser Lys Asn Leu Lys Ala
1               5                   10                  15

Arg Cys Ser Arg Lys Ala Leu His Val Asn Phe Lys Asp Met Gly Trp
                20                  25                  30

Asp Asp Trp Ile Ile Ala Pro Leu Glu Tyr Glu Ala Phe His Cys Glu
            35                  40                  45

Gly Leu Cys Glu Phe Pro Leu Arg Ser His Leu Glu Pro Thr Asn His
    50                  55                  60

Ala Val Ile Gln Thr Leu Met Asn Ser Met Asp Pro Glu Ser Thr Pro
65                  70                  75                  80

Pro Thr Xaa Cys Val Pro Thr Arg Leu Ser Pro Ile Ser Ile Leu Phe
                85                  90                  95

Ile Asp Ser Ala Asn Asn Val Val Tyr Lys Gln Tyr Glu Asp Met Val
            100                 105                 110

Val Glu Ser Cys Gly Cys Arg
        115
```

PROCESS FOR PREPARING PURIFIED ACTIVE MONOMER OF BONE-DERIVED FACTOR

RELATED APPLICATION DATA

This application is a Continuation-in-Part of U.S. patent application Ser. No. 10/414,954, filed Apr. 16, 2003 (now abandoned), which is a Continuation-in-Part of U.S. patent application Ser. No. 09/331,948, filed Jul. 7, 1999 (now U.S. Pat. No. 6,551,801), which is a 35 U.S.C. §371 national stage filing of PCT/JP97/04784, filed Dec. 24, 1997. U.S. patent application Ser. No. 10/414,954, is also a Continuation-in-Part of U.S. patent application Ser. No. 10/048,458, filed Feb. 6, 2002 (now U.S. Pat. No. 6,972,231), which is a 35 U.S.C. §371 national stage filing of PCT/EP00/07600, filed Aug. 4, 2000. U.S. patent application Ser. No. 10/414,954, is also a Continuation-in-Part of U.S. patent application Ser. No. 09/701,121, filed Jan. 3, 2001 (now abandoned) which is a 35 U.S.C. §371 national stage filing of PCT/IB99/00866, filed May 14, 1999. The entire contents of the related applications are hereby incorporated by reference.

FIELD OF THE INVENTION

This invention relates to a process for the production of a purified refolded monomeric or dimeric bone morphogenetic factor. More particularly, it is concerned with a process for the production of a refolded monomeric or dimeric bone morphogenetic factor, characterizing in acquiring a purified refolded monomeric or dimeric bone morphogenetic factor from an inclusion body produced by means of a genetic engineering technology.

BACKGROUND OF THE INVENTION

A proteinaceous bone morphogenetic factor was discovered to be present in the bone matrix (Science 150, pp.893-899, 1965) and was named as "bone morphogenetic protein" (hereinafter abbreviated as BMP). Recently, cloning of plural BMP-related genes has been attempted and it has been found that all of them (except BMP-1) belong to the transforming growth factor-β (hereinafter abbreviated as TGF-β) superfamily. Recombinants of some of these factors have been produced by means of a genetic engineering technology and they have been confirmed to have a bone morphogenetic activity, from which their application to the treatment of bone diseases is expected.

Of these factors, the human MP52 (GDF-5, CDMP-1) recently discovered and belonging to the human BMP family (Biochem. Biophys. Res. Commun., 204, pp. 646-652, 1994) has been confirmed by animal tests to be effective as a bone morphogenetic factor. Beyond cartilage and bone morphogenesis MP52 is known to be a multifunctional growth factor effective for example in angiogenesis (WO 95/04819, Yamashita et al. (1997) Experimental Cell Research 235, 218-226), neuronal diseases (WO 97/03188), periodontal and dental applications (WO 95/04819), connective tissue such as tendon and ligament (WO 95/04819, Rickert et al. (2001), Growth Factors 19, 115-126, Wolfman et al. (1997), Journal of Clinical Investigation 100 (2), 321-330) and skin related disorders such as wound healing or hair growth disorders (WO 02/076494). It has been technically reviewed to carry forward the large-scale production thereof by expression using recombinant *Escherichia coli* (*E. coli*).

However, when expressed in a large scale in *E. coli* and others, for instance, when the protein is produced at an amount of several grams per liter of cultured broth, the desired protein generally tends to form an inactive and insoluble inclusion body. This inclusion body comprises monomeric unfolded MP52 and, in order to obtain a dimer or a monomer which is active as a bone morphogenetic factor, the inclusion body must be solubilized, renatured and oxidized to a dimer or monomer of a defined three-dimensional structure (the procedure generally called "refolding"), separated and purified to obtain the desired protein.

The active form of MP52 has the following or the like problems:
1) because of its low solubility in an aqueous solution, it should be handled in the presence of a denaturing agent or under acidic conditions,
2) the protein used for separation tends to nonspecifically adsorb onto a resin for liquid chromatography and bind strongly to media such as ion-exchange or gel filtration, and
3) the surfactant essential for refolding tends to disturb separation, and thus it has been very difficult to establish a process for the purification thereof.

The purification process recently developed for obtaining a single active form of dimeric MP52 (WO 96/33215, see examples) comprises the following steps:
1. solubilizing an inclusion body by a denaturing agent,
2. separation by ion exchange chromatography in the presence of 6 M urea,
3. sulfonation,
4. separation by gel filtration chromatography in the presence of 6 M urea,
5. refolding in the presence of gluthatione,
6. recovery by isoelectric precipitation, and
7. separation by reverse-phase chromatography.

The purification process recently developed for obtaining a single active form of refolded monomeric MP52 (WO 99/61611, example 3) resembles that of the dimeric form and comprises the following steps:
1. solubilizing an inclusion body by a denaturing agent,
2. separation by ion exchange chromatography, in the presence of 6 M urea,
3. separation by gel filtration chromatography, in the presence of 6 M urea,
4. refolding in the presence of gluthatione,
5. recovery by isoelectric precipitation,
6. separation by r verse-phase chromatography,
7. isoelectric precipitation.

The WO 01/11041 also describes monomeric MP52 and its use and contains a purification process in the examples with the following steps:
1. solubilizing an inclusion body by a denaturing agent,
2. separation by reverse-phase chromatography,
4. refolding in the presence of gluthatione,
5. recovery by isoelectric precipitation,
6. separation by reverse-phase chromatography.

However, the above mentioned processes if scaled up industrially has have encountered some or all of the following and the like problems:
1) a large amount of a denaturing agent is used in order to solubilize the MP52 inclusion body and during purification steps using ion exchange or gel filtration columns because even the unfolded monomer needs constant presence of chaotropes such as 6 M urea, whereby modification of the protein (for example, carbamylation reaction in the case of urea) may be induced,
2) one or more purification steps are performed after solubilization prior to the refolding reaction, in part using an expensive resin for chromatography, especially, for gel filtration chromatography, such as Sephacryl S-20OHR or Superdex 200pg (all available from Pharmacia Biotech) is used in a large amount, 3) a reagent used in refolding, inter alia, oxidized glutathione essential for the refolding reaction is extremely expensive, and 4) when isoelectric precipitation is carried out after the refolding reaction, a dilution is necessarily performed to decrease the concentration of detergent, thus the volume of the solution is increased.

DISCLOSURE OF THE INVENTION

An object of this invention is to provide an improved and less expensive production process for bone morphogenetic factors by solving the above-mentioned problems, i.e., 1) to use a denaturing agent in an amount as low as possible;

2) to use a chromatography resin in an amount as low as possible;

3) to replace the reagent used for refolding by other inexpensive ones and to simplify concomitant procedures with refolding, 4) to decrease the volume of the solution by removing a detergent selectively; that is, to considerably shorten the process time.

The present inventors have made feasible a simplification of the purification steps by solubilizing an inclusion body extracted from E. coli in the presence of a denaturing agent, conducting a direct refolding according to a dilution procedure and then subjecting an ultrafiltration substituting the refolding solution. The term "direct refolding" means that the refolding reaction is performed directly after solubilization of the inclusion body without prior purification. This procedure appears to be similar to the first step of a process for the production of human insulin from E. coli (EP 600372A1). However, since a bone morphogenetic factor is different in properties from a soluble protein such as human insulin, it was difficult to apply the process for the production of insulin as depicted above in case of a bone morphogenetic factor. MP52 (active form) as depicted above has a low solubility and tends to adsorb onto a chromatographic resin, thus in the large-scale production, the ion exchange chromatography or hydrophobic chromatography used for human insulin or the gel filtration chromatography used in the above-mentioned WO 96/33215 could not be applied. When an ion exchanger (SP Sepharose FF, Pharmacia Biotech) is used, for example, MP52 is not completely eluted because of its strong adsorption onto the resin, even if a denaturing agent and a maximum salt concentration is used. When gel filtration (Sephacryl S-20OHR, Pharmacia Biotech) is used, a strong adsorption of the protein onto a resin occurs even if a denaturing agent is used, causing an excessively broadened fractionation range and thus a very poor separation. Further, properties of the resin are altered by influence with of a surfactant such as CHAPS, which leads to loss of reproducibility. This is also applicable to the elution with an acidic solution in which MP52 is soluble. In conclusion, it is not feasible to make use of the original properties of the resin.

As explained above, it has become apparent that the purification of the desired protein in large-scale production can not be accomplished according to a general chromatographic means using aqueous system. Reverse-phase chromatography using organic solvent is the only means that could be utilized. In view of this, it was necessary to develop a purification means wherein many columns are not used. As purification means other than using columns, a fractionating method by ammonium sulfate seemed promising. However, since it had low purification efficiency and led to unnecessarily low yield, its use was cast aside. In addition, isoelectric precipitation procedure by pH adjustment was adopted, but prior to the actual procedure, an ultrafiltration procedure to remove a surfactant, CHAPS, was carried out which enabled the performance of isoelectric precipitation without increasing the volume of the solution. Conventionally, when the solution contained CHAPS, the protein solubility was high and no precipitation occurred. Therefore, a dilution was necessary to decrease the concentration of CHAPS, but a resultant extensive increase in solution volume has been a problem in process development.

This invention is directed to a process for the production of a purified refolded monomeric or dimeric bone morphogenetic factor, characterized by introducing the polynucleotide encoding a bone morphogenetic factor into a bacterium such as E. coli, expressing said bone morphogenetic factor in form of an inclusion body, recovering said inclusion body, preferably washing the inclusion body and subjecting said inclusion body of a bone morphogenetic factor to the following steps a)-c) in order, thereby producing an active monomeric or dimeric bone morphogenetic factor and subsequently purifying it;

a) treating an inclusion body of a bone morphogenetic factor with a denaturing agent to obtain a solubilized monomer, b) treating the solubilized monomer directly with a refolding solution to obtain an active monomeric or dimeric bone morphogenetic factor, c) subjecting the refolded monomeric or dimeric bone morphogenetic factor to purification.

Purification can be reached by a) treating the active refolded monomeric or dimeric bone morphogenetic factor by ultrafiltration and substitution of solvent, b) subjecting the active refolded monomeric or dimeric bone morphogenetic factor to one or more isoelectric precipitation steps, and c) subjecting the active refolded monomeric or dimeric bone morphogenetic factor thus precipitated to one or more reverse-phase chromatography steps.

The inclusion body of a bone morphogenetic factor produced by means of a genetic engineering technology is preferably the one expressed in E. coli by means of a genetic engineering technology.

When a bone morphogenetic factor is expressed in E. coli, the cells are suspended in a buffer, homogenized by standard techniques such as a homogenizer or sonification and centrifuged to recover an inclusion body. The inclusion body is washed with a buffer containing a detergent, for example, Triton X-100, or a denaturing agent such as urea or guanidine-HCl, in a concentration which does not yet solubilize the bone morphogenetic factor to a significant extent (for example 1 M urea). The washing step is preferably repeated one, two, three or more times and centrifuged to obtain an inclusion body of primary purification.

The step in which an inclusion body of a bone morphogenetic factor is treated with a denaturing agent to give a solubilized monomer may be carried out by adding the inclusion body to a solution containing the denaturing agent and dissolving by stirring. For the solution containing a denaturing agent, any of those publicly known such as 8 M urea or 6 M guanidine-HCl and others in a buffer such as 50 mM glycine-NaOH buffer (pH 10.7) may be used.

The step in which a solubilized monomer is treated with a refolding solution to give an active refolded monomer or dimer is carried out by diluting the protein solution obtained above with a refolding buffer. The refolding conditions of this invention allow high protein concentrations even above 1.0 mg/mL. Therefore the final protein concentration during the refolding reaction is between 0.01 and 5.0 mg/mL, preferably above 0.1 mg/mL. These are very high protein concentrations (other refolding processes use typically several µg/ml) which are of great industrial importance because of reduced process volumes. Although dilution has been hitherto made so as to provide a final concentration of a denaturing agent to 1M or less, it is preferable in this invention that the dilution be made so as to provide a final concentration of a denaturing agent between 1 and 4 M, particularly, 2.4 M, so that aggregation and precipitation of proteins may be prevented with an improved yield. For the refolding solution, any of those publicly known in the prior art be used. For example surfactants, e.g., cholic acid or its derivatives such as 3-[(3-cholamidopropyl)dimethylamonio]-2-hydroxy-1-propanesulfonate (CHAPSO), taurocholic acid or a salt thereof, taurodeoxycholic acid or a salt thereof, and preferably, 3[(3-cholamidopropyl)dimethylammonio]-1-propanesulfonate (CHAPS). Cholic acid or its derivatives are preferably used in a final concentration of 5 to 100 mM. Especially preferred is a CHAPS concentration of approximately 20 mM which minimizes the substitution rate prior to isoelectric precipitation without lowering the yield. Furthermore the refolding solution may comprise EDTA and sodium chloride (preferably at a final concentration of 0.1 to 1.5 M). In addition a combination of a reducing agent such as mercaptoethanol or dithiothreitol (DTT) with oxidized glutathione or a buffer containing cysteine or the like may be used. Cysteine is preferably used. The advantage of using cysteine alone is that it is not necessary to use generally expensive oxidizing reagent and that it can decrease its amount of use. Therefore, it is expected to simplify the process steps and to save the cost for reagents. Cysteine in the refolding solution is preferably used in a final concentration between 0.8 and 4.8 mM per 0.8 mg/ml protein, more preferably in a concentration of approximately 1.6 mM per 0.8 mg/ml protein. Using for example a final protein concentration of 2.4 mg/ml in the refolding solution, cysteine would be preferably used in a final concentration of about 4.8 mM. Cysteine is preferably added already to the solubilized inclusion body or is contained in the solubilization buffer in order to break existing disulfide bonds. During dilution of the solubilized inclusion body with a refolding buffer cysteine reaches its final concentration in the refolding solution which allows the oxidation of disulfide bonds and is favorable for the MP52 refolding. The addition of an oxidizing agent is unnecessary.

The reagent contained in the refolding solution other than above described is that having a guanidino group which also prevents a protein aggregation and precipitation and allows the use of high protein concentrations with increased yield. More specifically, guanidine hydrochloride or arginine hydrochloride (ArgHCl), preferably 0.5 M of Arg-HCl is added to the refolding solution in advance. The effect of the addition of Arg-HCl is shown in Table 1.

TABLE 1

| Protein concentration (g/L) | MP52dimer (g/L) |
|---|---|
| 0.8* + 0.5M Arg-HCl | 0.37 |
| 1.6 + 0.5M Arg-HCl | 0.62 |
| 2.4 + 0.5M Arg-HCl | 0.98 |
| 3.2 + 0.5M Arg-HCl | 0.95 |
| 2.4 without Arg-HCl | protein aggregation occurred |

*Protein concentration of 0.8 g/L was the upmost limit for the protein concentration without Arg HCl.

As shown in Table 1, without Arg-HCl, protein aggregation and precipitation occurred in the refolding solution. However, by adding Arg-HCl, the amount of protein that can be treated per refolding solution without aggregation can be increased by 2.7 fold (i.e. 0.98 g/L as opposed to 0.37 g/L).

As for a buffer, those buffers using phosphate, Tris-HCl or Glycine-NaOH may be used, but an Arg-NaOH or a buffer comprising Arg-NaOH and Glycine-NaOH is preferred. The pH should be in the range between pH 8 and 10, preferably between pH 8.5 and 9.5, particularly most preferably pH 8.9.

The ultrafiltration step is performed using a membrane which retains the refolded MP52. The ultrafiltration step, in which the refolded dimer is concentrated, is carried out by using preferably a molecular weight cut-off membrane filter of 10,000 such as PSU 10K (Sartorius). The ultrafiltration step in which the refolded monomer is concentrated, is carried out by using preferably a molecular weight cut-off membrane filter up to 10.000 and especially preferred of 5,000 (5K). The CHAPS concentration is lowered by substituting with an acid solution, such as 0.2% phosphoric acid solution.

The step in which the solution of the dimer or monomer substituted is isoelectrically precipitated, is carried out by adding alkali solution such as NaOH or a buffer to the dimer or monomer solution in order to adjust the pH value to selectively precipitate a bone morphogenetic factor. The pH value for the dimeric MP52 is preferably in the range between pH 6.5 and 8.0 and especially preferred pH 7.4. The refolded monomeric bone morphogenetic factor can be subjected to isoelectric precipitation using preferably a pH range between pH 6.5 and 7.5 (WO 99/61611) and especially preferred pH 7.1. After the pH adjustment, the solution is allowed to stand for one hour or more, centrifuged or filtered to remove the supernatant and the precipitate is dissolved in an acid solution such as 50 mM citric acid, 0.2% phosphoric acid or 0.05% trifluoroacetic acid solution.

The step in which the isoelectrically precipitated dimer or monomer is subjected to reverse-phase chromatography, is carried out by subjecting the acidic solution obtained above to high-performance liquid chromatography and eluting with gradients (for example 0-50%) of organic solvent such as isopropanol, acetonitrile or ethanol with an acid (such as phosphoric acid, citric acid, hydrochloric acid, trichloracetic acid, heptafluorobutyric acid, trifluoroacetic acid) in the elution solvents to recover the fractions of refolded monomeric or dimeric bone morphogenetic factor. A preferred solvent system is ethanol-phosphoric-acid. Preferably a linear gradient of 0 to 50% ethanol with 0.2% phosphoric acid in the elution solvents is used. As resin for high-performance liquid chromatography, those known in the art may be used. A polymeric resin such as SOURCE 15 RPC (6 cmφ×20 cm, manufactured by Pharmacia Biotech) is preferably used.

The bone morphogenetic factor to be used in this invention is a protein of the TGF-β superfamily with bone morphogenetic activity, preferably a bone morphogenetic factor having a single molecular weight selected from the group consisting of MP52, BMP-2, BMP-4, BMP-6, BMP-7, BMP12 and BMP13. MP52 is especially preferred. The term "bone morphogenetic factor" as used in this invention comprises the monomeric and dimeric mature proteins as well as active variants thereof. These variants are preferably fragments retaining activity, mature proteins containing conservative amino acid substitutions, proteins showing at least 70% homology ((homology in the present invention means that amino acids within the following groups are homolog: "S, T, P, A, G" and "N, Q, D, E" and "H, R, K" and "M, I, L, V" and "F, Y, W" not counting gaps due to the sequence alignement) and preferably 70% identity to the mature wild-type proteins.

The bone morphogenetic factors are well known proteins and several active variants are published yet. For example it is known, that the 7 cysteine region containing the 7 conserved cysteines among members of the TGF-β family is important for the 3-dimensional structure and is considered to be the most important part of the proteins in view of the biological activity. For MP52 the 7 cysteine region starts with the cysteine at position 18 of SEQ ID NO. 1. Deviations at the N-terminal part do not effect its activity to a considerable degree. Therefore, substitutions, deletions or additions on the N-terminal part of the proteins are still within the scope of the present invention. For variants of MP52 see for example (WO 95/04819, WO 96/33215, WO 97/04095, WO 01/11041).

It is disclosed in the state of the art that members of the TGF-β superfamily, such as bone morphogenetic factors, form a defined structure by intramolecular disulfide bonds of six of the conserved 7 cysteines known as the cysteine knot. One cysteine of the conserved 7 cysteines forms an intermolecular disulfide bond with the corresponding cysteine of the second monomer subunit thereby forming a dimer (Schlunegger & Grutter (1992) Nature 358, 430-434; Daopin et al. (1992) Science 257, 369-373; Griffith et al. (1996) Proc. Natl. Acad. Sci. 93, 878-883 and Venkataraman et al. (1995) Proc. Natl. Acad. Sci. 92, 5406-5410). For producing active refolded monomeric bone morphogenetic factor, the latter cysteine, responsible for dimer formation, is preferentially deleted or substituted by another amino acid. The another amino acid can be selected by any amino acid that does not impair the formation of a biologically active confirmation. It is preferably selected from the group of alanine, serine, threonine, leucine, isoleucine, glycine and valine. The most preferred protein is the monomeric MP52. A variant of the mature MP52, with a missing alanine at the N-terminus, is shown in SEQ. ID. NO. 1. The position of the cystein which normally forms the intermolecular disulfide bridge and is deleted or substituted by another amino acid for producing the monomeric form is shown as a "X". For a more detailed description of monomeric proteins see WO 01/11041.

As an example for dimeric MP52, the *E. coli* strain having introduced therein cDNA encoding a human MP52 protein (specifically, the *E. coli* having introduced therein a plasmid ligated with a codon encoding methionine at the 5-primer terminus in MP52-sequence of 119 residues of which the N-terminal alanine of mature human MP52 is deleted, see SEQ ID NO. 1 with "X" at position 83 being a cysteine for this MP52 variant) is incubated to produce mature monomeric MP52 as inclusion body in large amounts and using the present process, mature dimeric MP52 is obtained with high purity from this inclusion body.

As an example to get a refolded monomeric MP52 without competitive formation of the active dimeric form, the cysteine residue responsible for the intermolecular disulfide bridge between two monomers was replaced by an alanine residue (see SEQ ID NO. 1 with "X" at position 83 being an alanine for this MP52 variant). This human MP52 variant was named MP52-Ala83. It consists of 119 amino acids (the N-terminal alanine of the mature MP52 is deleted) and was produced as inclusion bodies in *E. coli*, refolded and purified to give active refolded monomeric MP52.

BRIEF DESCRIPTION OF THE SEQUENCE AND DRAWINGS

SEQ ID NO:1 shows the amino acid sequence of a preferred human MP52 variant. It is the mature form with a missing alanine at its N-terminus consisting of 119 amino acids. For producing active dimeric MP52 according to the present invention, "X" is a cysteine. For producing active monomeric MP52 according to the present invention, "X" is any amino acid preferably except cysteine, and especially preferably alanine, serine, threonine, leucine, isoleucine, glycine or valine.

FIG. 1 shows a silver stained polyacrylamid gel isolated inclusion body after expression of monomeric MP52-Ala83 in *E. coli*, homogenization in the presence or absence of Triton X-100 and sonification and wash with a buffer containing 1 M urea.

Figure 2:
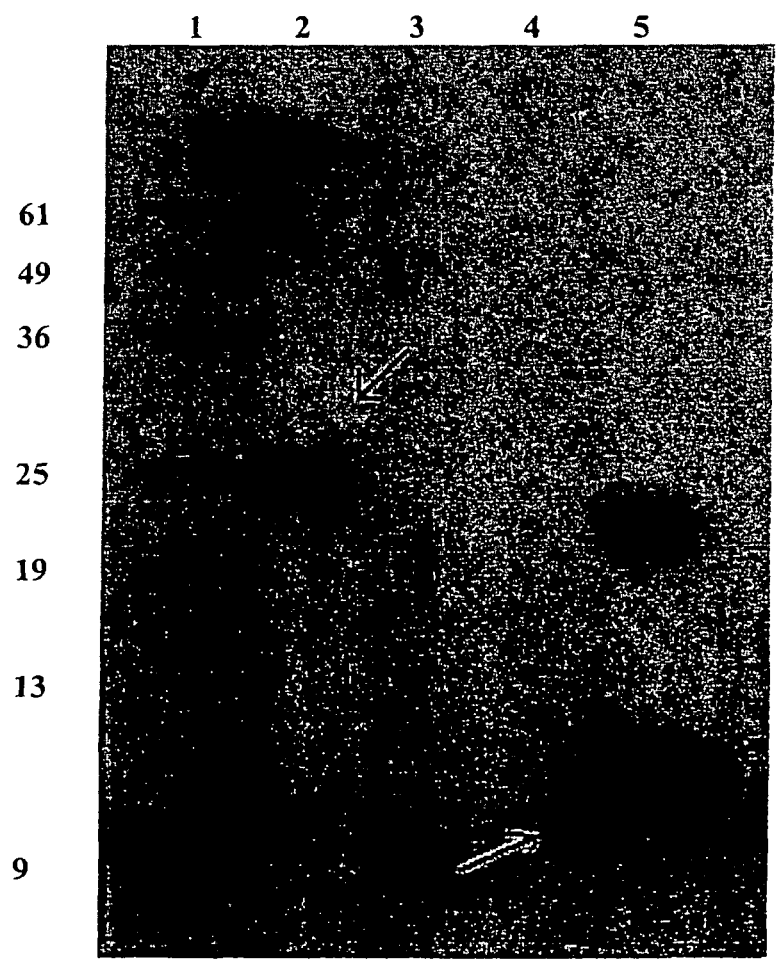

1. Molecular weight marker in kD (Novagen Perfect Protein Marker, Cat. No. 69149-1)
2. positive control: 0.05 µg MP52 (expressed, refolded and purified according to WO 96/33215) in the presence of DTT in the monomeric form.
3. 0.12 µg isolated inclusion bodies (in the presence of DTT) containing monomeric MP52-Ala83 after homogenization and wash.
4. 0.21 µg isolated inclusion bodies (in the presence of DTT) containing monomeric MP52-Ala83 after homogenization and wash
5. 0.15 µg isolated inclusion bodies (in the presence of DTT) containing monomeric MP52-Ala83 after homogenization in the presence of Triton-x-100 and with sonification and wash
6. 0.22 µg isolated inclusion bodies (in the presence of DTT) containing monomeric MP52-Ala83 after homogenization in the presence of Triton-x-100 and with sonification and wash FIG. 2 shows a western blot for demonstrating successful refolding of monomeric MP52 (MP52-Ala83) after isolation and solubilization of inclusion body. The antibody (aMP5) used detects oxidized refolded monomer or dimer but not reduced unfolded monomeric MP52.

Figure 3:

1. Marked molecular weight marker in kD (Gibco BRL Protein Ladder, Cat.-No. 10748-010)
2. positive control: refolded dimeric MP52 (marked by an arrow) expressed, refolded and purified according to WO 96/33215.
3. isolated inclusion bodies containing MP52-Ala83 after expression and homogenization.
4. solubilized inclusion bodies containing MP52-Ala83
5. monomeric MP52-Ala83 (marked by an arrow) after direct refolding FIG. 3 shows a western blot (using the antibody aMP5) for demonstrating the presence of monomeric MP52 (MP52-Ala83) during different purification steps.

1. Marked molecular weight marker in kD (Gibco BRL Protein Ladder, Cat. No. 10748-010)
2. positive control: refolded dimeric MP52 (20 ng)
3. monomeric MP52-Ala83 after ultrafiltration and isoelectric precipitation, starting material for the semi-preparative reverse phase HPLC (3 µl)
4. flow through of the semi-preparative reverse phase HPLC (20 µl)
5. wash out of the semi-preparative reverse phase HPLC (20 µl)
6. fraction 21 of the semi-preparative r verse phase HPLC (10 µl)
7. fraction 22 of the semi-preparative reverse phase HPLC (5 µl)
8. fraction 23 of the semi-preparative reverse phase HPLC (10 µl)
9. fraction 24 of the semi-pr parative r verse phase HPLC (10 µl)
10. fraction 25 of the semi-preparative reverse phase HPLC (10 µl)

11. fraction 26 of the semi-preparative reverse phase HPLC (10 μl)

Figure 4:
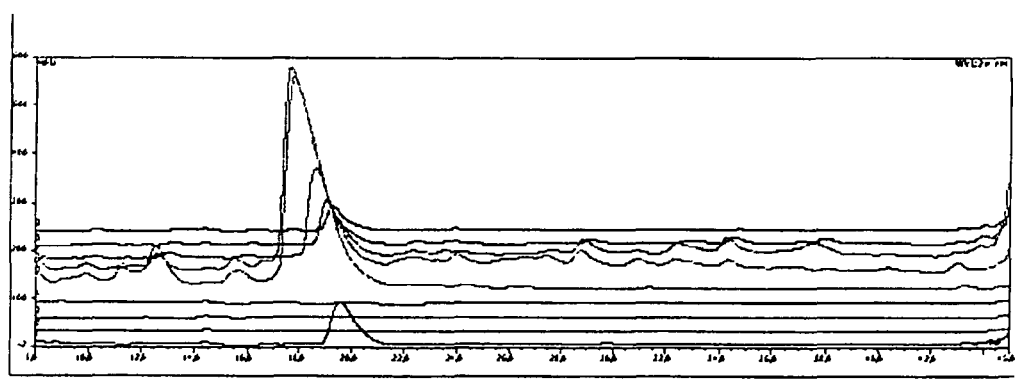

FIG. 4 shows superimposed elution profiles of analytical reverse-phase HPLC showing the fractions of the semi-preparative reverse-phase HPLC (lane 4=fraction 21, lane 5=fraction 22, lane 6=fraction 23, lane 7=fraction 24, lane 8=fraction 25, lane 9=fraction 26,) as well as the starting material (lane 1, MP52-Ala83 expressed in E. coli, directly refolded from solubilized inclusion bodies, purified by ultrafiltration and isoelectric precipitation), the flow through (lane 2) and the wash (lane 3) of the preparative reverse-phase HPLC.

Figure 5:
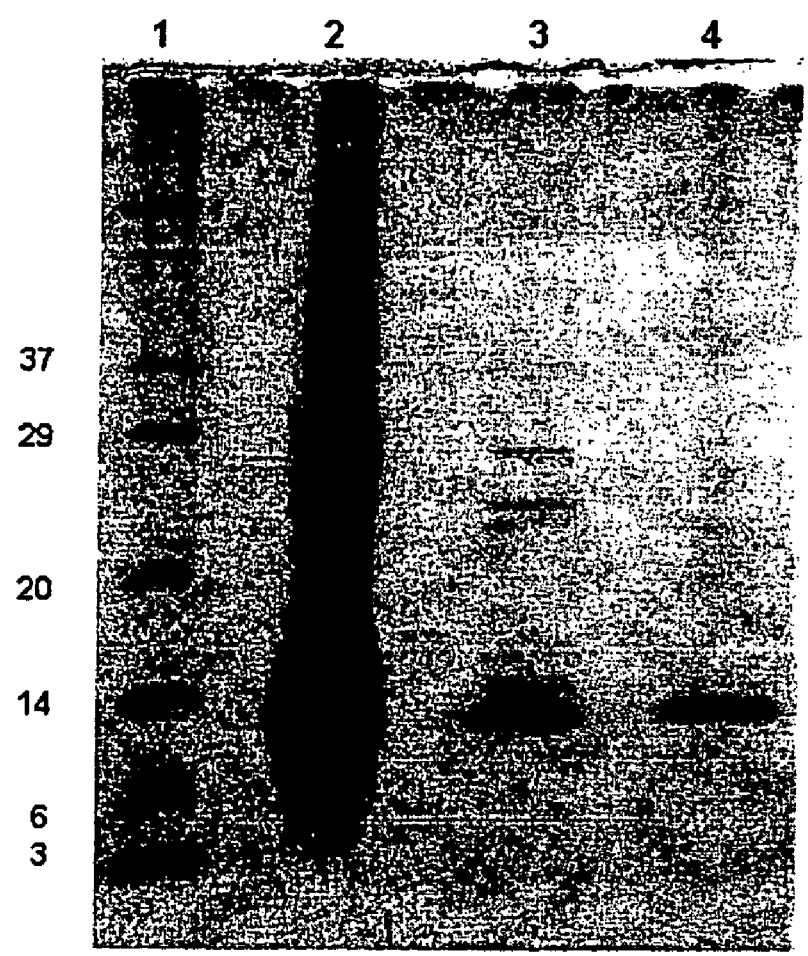
Figure 6:
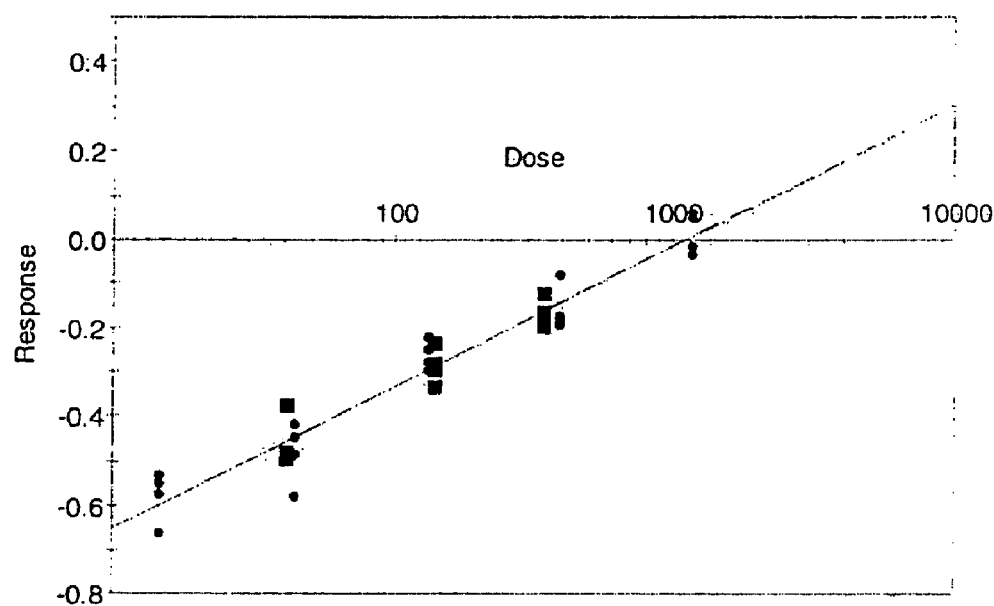

FIG. 5 shows the different steps of a typical purification of monomeric MP52-Ala83 analyzed on a silver stained polyacrylamid gel.
1. Molecular weight marker in kD (Protemix MWM (Anamed), 0.5 μl
2. 1 μg isolated inclusion bodies containing monomeric MP52-Ala83 after homogenization and wash
3. 0.5 μg monomeric MP52-Ala83 after ultrafiltration and isoelectric precipitation
4. 0.5 μg monomeric MP52-Ala83 after reverse phase chromatography FIG. 6 shows the result of an alkaline phosphatase (ALP) assay whereby "response" means the measured absorbance at 405 nm converted into logarithmic results ($\log_{10}$) and "dose" means the concentration of MP52 (ng/ml). Obviously the activity of refolded monomeric MP52 (squares), expressed, refolded and purified according to the present invention is about the same as the activity of dimeric MP52 (circles) expressed, refolded and purified according to the WO 96/33215.

EXAMPLES

This invention will be more specifically explained herein below by way of examples, which are not construed to limit the Invention. The procedures from (2) to (4) were carried out in a low temperature chamber at 4° C., considering stability of the protein. The steps (1) to (5) describe expression, direct refolding and purification in order to get refolded dimeric MP52 with biological activity. The steps (6) to (9) describe likewis the expression, direct refolding and purification in order to g t refolded monomeric MP52 with biological activity.

Each step will be fully explained below.

(1) Fermentation of Human MP52 and Primary Purification of Inclusion Body

The MP52-producing E. coli, obtained in the same manner as described in Example 2 of WO 96/33215, was precultivated in a modified SOC medium and then the precultivated broth was inoculated into 100 L of production medium. For induction, 1 mM isopropyl-β-D-thiogalactopyranoside (IPTG) was added at an early logarithmic growth phase and fermentation was continued at 32° C. until $OD_{550}$=150. After that, cells were harvested, cells were suspended in a buffer containing 25 mM Tris-HCl (pH 7.3) and 10 mM EDTA-4Na, homogenized by means of a homogenizer (manufactured by Manton Gaulin) and centrifuged to recover an inclusion body. The inclusion body was washed with a buffer containing 1 M urea as a detergent and centrifuged to obtain an inclusion body with primary purification applied.

(2) Solubilization of Inclusion Body and Refolding

One hundred g (wet weight) of the inclusion body obtained above was solubilized by stirring in 300 mL of 50 mM glycine-NaOH buffer containing 8 M urea and 5 mM ethylenediamine-tetraacetate (pH 8.9) (protein concentration being about 18 mg/mL). Refolding was performed by diluting the inclusion body solution with a refolding buffer [0.5 M Arg-NaOH (pH 8.9), 4.8 mM cysteine hydrochloride monohydrate, 0.5 M sodium chloride, 20 mM CHAPS] to 6.7 times volume (final protein concentration being about 2.4 mg/mL). The mixture as such was allowed to stand at 4° C. for about 20 hours.

(3) Purification of MP52 after Refolding (Ultrafiltration)

MP52 after completion of the refolding reaction was concentrated 5 fold by using a membrane filter of 10,000 cut-off molecular weight (PSU 10K, Sartorius) and the solution was diluted and substituted by 5 fold volume with 0.2% phosphoric acid solution. By repeating the procedure three times, the CHAPS concentration is diluted theoretically by 100 fold or more.

(4) Purification of MP52 after Refolding (Isoelectric Precipitation)

Isoelectric precipitation was performed by adding NaOH solution to the substituted refolding solution adjusting the pH value to 7.4. The solution became cloudy, and then it was allowed to stand for one hour or more. Then it was centrifuged (10,000 g×15 min) and the precipitate was recovered. The precipitate was dissolved in 0.2% phosphoric acid solution.

(5) Purification of MP52 after Refolding (Reverse-Phase Chromatography)

MP52 dissolved in the phosphoric acid solution was separated by means of reverse-phase chromatography. A high-performance liquid chromatographic system using SOURCE 15 RPC (6 cmφ×20 cm, Pharmacia Biotech) as resin was operated and eluted with 0-50% ethanol gradient to recover the fractions containing dimeric MP52.

According to the above mentioned purification process, we have succeeded in recovering an active form of MP52 in high yield as shown in Table 2. An amount of MP52 in the purification step was determined by quantification of scanned CBB-stained-electrophoresis gel image.

TABLE 2

| Step | Amount of MP52 (g) | Yield |
| --- | --- | --- |
| Solubilization | 5.4 | 100 |
| Refolding | 2.2 | 41 |
| Ultrafiltration | 1.6 | 30 |
| Isoelectric precipitation | 1.5 | 29 |
| Reverse-phase chromatography | 1.1 | 21 |

(6) Fermentation of Human Monomeric MP52-Ala83 and Primary Purification of the Inclusion Body In order to get a monomeric MP52 in high yield without competetive formation of the refolded dimeric form, the cysteine residue responsible for the intermolecular disulfide bond between two monomers, was replaced by an alanine residue (position 83 in SEQ ID NO.1). This mutated human MP52 was named MP52-Ala83. The human monomer expression vector pKOT279 (2.9 kb), described in detail in example 1 of WO 99/61611 and deposited at the International Depository Authority under Budapest treaty on Feb. 3, 1999 (Deposit No. FERM BP-6637) was introduced in E. coli W3110M and cultivated essentially as described in example 2 of WO 99/61611 or as described in example 2 of WO 96/33215. However, during trial expressions the culture volume was reduced to 2 l or less such as 100 ml without regulating the pH and oxygene concentration. The cells wer harvested by centrifugation and suspended in a homogenization buffer containing 25 mM Tris-HCl (pH 7.3) and 10 mM EDTA (1 g cells (wet weight) per 10 ml). The suspension was treated three times in a nitrogen pressure bomb (model 4639 from Parr) using 1500-2000 Psi and 0° C. in order to break the cells. Alternatively homogenization can be reached by using extensive sonification, a homogenizer or combinations thereof. Adding 1% Triton-X (final concentration) to the homogenization buffer and subsequent sonification can improve the removal of foreign cell proteins from the inclusion body containing MP52 as shown in FIG. 1. The inclusion body was recovered by centrifugation at 4° C., resuspended in a washing solution containing 1 M Urea and a buffer such as 20mM Tris pH 8.3 and 5 mM EDTA. The washing step was repeated once. Successful trial expression (100 ml) of monomeric MP52 is seen in FIG. 1. FIG. 1 reveals that the isolated and washed inclusion bodies already contain predominantly the recombinant MP52 and only little impurity protein components. The expression level can be improved further in large scale expression with regulated pH and oxygene concentration.

(7) Solubilization of Inclusion Body and Direct Refolding.

The washed inclusion body obtained above by a 4 l expression was solubilized by stirring in 50 mM glycine-NaOH buffer (pH 8.9) containing 8 M Urea, 5 mM EDTA and 32 mM cysteine (about 1 g inclusion body (wet weight) per 3 ml). Solubilization may be supported by sonification. The resulting protein concentration was about 16 mg/ml depending on the expression and homogenization method. The solubilized inclusion body solution was diluted 6.7 times (for example in trial purifications 6 ml solubilized inclusion body solution plus 34 ml refolding buffer) using a refolding buffer containing arginine-NaOH (pH 8.9), NaCl, CHAPS and additional urea. The final concentration of arginine-NaOH (pH 8.9) and NaCl in the refolding solution were 0.5 M each, that of CHAPS 20 mM. Due to the dilution (6.7 times) the final concentration of cysteine-HCL in the refolding solution was 4.8 mM, that of EDTA 0.75 mM and that of glycine-NaOH buffer (pH 8.9) 7.5 mM. The final concentration of urea in the refolding solution was adjusted to 2.4 M. The final protein concentration in the refolding solution was about 2 mg/ml protein (solubilized inclusion body). This refolding solution was allowed to stand (without stirring) at 4° C. for about 20 hours. The refolding was controlled by a western blot using standard conditions. The antibody used was the mouse anti-human MP52 monoclonal antibody aMP-5 which is described in detail in the EP 0 919 617. This antibody is able to bind to refolded dimeric human MP52, but not to the reduced unfolded monomeric MP52. Nevertheless this antibody detects also the refolded monomeric MP52. Therefore the antibody aMP-5 detects only oxidized and folded, but not reduced and unfolded MP52. For the western blot the antibody was used in a concentration of 0.6 µg/ml. The result of the refolding process is shown in FIG. 2. The unfolded monomeric MP52 in the inclusion body and monomeric MP52 after solubilization of the inclusion body was not detected by this antibody as expected. After direct refolding the refolded monomeric MP52 is visible (marked by an arrow). Besides the desired refolded monomeric MP52 an additional band appears which probably belongs to oligomeric side products (possibly not correctly folded dimer) and which is removed during subsequent purification steps (see FIG. 3). As a positive control, dimeric MP52 (marked by an arrow) is shown.

(8) Purification of Monomeric MP52 after Refolding

Solvent exchange was reached by using an ultrafiltration membrane (diafiltration). Thereby the CHAPS of the refolding solution was removed to below the critical micellar concentration which is advantageously because CHAPS could disturb the isoelectric precipitation as well as the binding of MP52 to the hydrophobic reverse-phase media.

Therefore the refolded solution was concentrated fivefold using a membrane filter with a 10,000 cut-off molecular weight (Pall OMEGA 10K, OMO10076) and diluted fivefold with 0.2% phosphoric acid solution at 4° C. Alternatively a membrane filter with a 5,000 cut-off molecular weight (Pall Filtron 5K, OMO05076) was used. Membrane filters with a molecular cut off of 10.000 may have a loss of up to 10% of the refolded monomer. This concentration and dilution process was repeated twice so that the final CHAPS concentration was diluted theoretically 100 fold or more.

Isoelectric precipitation was performed by adding NaOH solution to the substituted refolding solution adjusting the pH value to about 7.4. Precipitation was allowed for about 1 hour at 4° C. Subsequently it was centrifuged (10,000 g×15 min, 4° C.). The precipitate was recovered and dissolved in 0.2% phosphoric acid solution.

Refolded monomeric MP52 in the 0.2% phosphoric acid containing solution was for the present separated by semi-preparative reverse-phase chromatography. The protein solution ((8 ml, about 1 mg, combined with 2.5 ml 0.1% trifluoroacetic-acid) was loaded on a column (Vydac 214TP104, C4), washed with equilibration solution (12 ml) and eluted with a linear gradient (3% /min) acetonitril with 0.1% trifluoroacetic acid. Fractions of 2 ml each were collected. However, for preparative purposes and clinical use of the resulting purified monomeric MP52 a reverse phase essentially as described for the dimeric protein using ethanol and phosphoric acid as a solvent system is preferred. Although the acetonitril-trifluoroacetic-acid solvent system is efficient, it should be avoided because of toxicity. Some fractions of the semi-preparative reverse-phase chromatography as well as the starting material (MP52-Ala83 expressed in E. coli, directly refolded from solubilized inclusion bodies, purified by ultrafiltration and isoelectric precipitation), the flow through and the wash were analyzed on an analytical HPLC (Vydac 218TP52, C18, acetonitril with 0,15% trifluoroacetic acid) (FIG. 4) and in western blot analysis (FIG. 3). As can be seen from FIG. 3 and FIG. 4, there is no significant loss of monomeric MP52 in the flow through or wash. As confirmed by western blot analyses monomeric MP52 was primarily in fractions 22 and 23 and to a continually lesser extent in fractions 24 to 26 (FIG. 3). However, in order to get a refolded monomeric MP52 of very high purification useful for clinical purposes it may be necessary to perform an additional purification step. For example it is possible to perform an additional isoelectric precipitation after the reverse-phase chromatography. Another possibility would be the use of a second reverse phase column with a different solvent system. A purification step to remove residual endotoxins may be useful too.

(9) Measurement of Biological Activity of Purified Refolded Monomeric MP52

The activity was measured in vitro by quantification of alkaline phosphatase (ALP) activity using the established mouse cell line MCHT-1/26. The cells were incubated for 3 days in alpha-MEM medium containing 10% FCS, L-Glutamine (20 mM) and penicillin/streptomycin to a confluence of less then 95%. The washed, trypsin treated cells were resuspended in the same culture medium and dispensed in 96-well microtiter plates ($4.5 \times 10^3$ cells per well).The cells were allowed to adhere for 24 hours, washed (alpha-MEM containing L-Glutamine (20 mM) and subjected to various concentrations of MP52 (each concentration 4 times) diluted in culture medium. Fraction 22 of the preparative reverse phase HPLC, containing most of the refolded monomeric MP52 was diluted to the following concentrations: 400 ng/ml, 133.2 ng/ml, 44.5 ng/ml. It was compared to a standard of dimeric MP52 (expressed, refolded and purified according to the WO 96/33215, concentrations: 1200 ng/ml, 400 ng/ml, 133.2 ng/ml, 44.5 ng/ml, 14.8 ng/ml and the negative control contained no MP52), for which the in vivo bone formation activity has been determined. The cells were incubated for 72 hours, washed and lysed by incubation in 0.2% Nonidet P-40 d tergent and 1 mM MgCl$_2$ over night. The supernatant was mixed with p-nitrophenylphosphate, the substrate for alkaline phosphatase, and the reaction stopped after 1 hour at 37° C. Changes in absorbance at 405 nm were measured and used for the calculation of the relative biological activity by the help of the programs DELTA SOFT, EXCEL and PARALLEL PRO. Thereby OD 405 results were converted into logarithmic results (log$_{10}$) and are shown in FIG. 6 as the "response". The term "dose" means the concentration of MP52 (ng/ml). As can be seen from FIG. 6, the activity of refolded monomeric MP52 (squares), expressed, refolded and purified according to the present invention is about the same as the activity of dimeric MP52 (circles) expressed, refolded and purified according to the WO 96/33215.

Therefore it is possible to recover active monomeric MP52 in high yield using the above mentioned refolding and purification process.

One of the advantages of the purification process in this invention is an effective reduction of the purification cost.

According to a preliminary calculation, the total process cost may be reduced to about ½ per protein as compared with those in WO96/33215 or WO 99/61611. Therefore, the present purification process can be very useful in industrialization.

According to the present process, an active refolded monomeric or dimeric bone morphogenetic factor having a single molecular weight can be efficiently produced in a large amount and more inexpensively, as compared with the prior art process.

The active refolded monomeric or dimeric bone morphogenetic factor obtained by the present process can be used in any known applications for bone morphogenetic factors. These are not only applications where cartilage or bone morphogenesis is advantageous but many other applications (see for example WO 92/15323). For example MP52 may be used for the repair of damaged or diseased cartilage and bone, for dental and periodontal applications, for the repair of connective tissue such as tendon and ligament, for neural applications, for applications where angiogenesis is advantageous as for example after stroke or ischemia, for skin related disorders and for wound healing and tissue repair. For a more detailed description of possible applications for MP52 see for example WO 95/04819, WO 96/33215, WO 97/04095, WO 01/11041, in WO 99/61611, WO 97/03188, WO 98/21972, WO 96/39169, WO 95/16035, WO 02/076494, WO 94/15949 and WO 96/14335.

```
SEQ ID NO 1:
PLATRQGKRP SKNLKARCSR KALHVNFKDM GWDDWIIAPL

EYEAFHCEGL CEFPLRSHLE PTNHAVIQTL MNSMDPESTP

PTXCVPTRLS PISILFIDSA NNVVYKQYED MVVESCGCR
```

---

We claim:

1. A process for producing a purified refolded monomeric MP52, comprising
   a) expressing a monomeric MP52 in the form of an inclusion body in *E. coli* and recovering said inclusion body;
   b) treating the recovered inclusion body with a denaturing buffer to obtain a solubilized monomeric MP52;
   c) treating the solubilized monomeric MP52 directly with a refolding solution to obtain a refolded monomeric MP52; and then
   d) subjecting the refolded monomeric MP52 to purification;
   wherein the monomeric MP52 contains an amino acid sequence as set forth in SEQ. ID. NO: 1 wherein X in SEQ. ID. NO:1 is not cysteine; and wherein the purified and refolded monomeric produced in step d) is biologically active; and wherein the denaturing buffer contains cysteine.

2. The process of claim 1, wherein the refolded monomeric MP52 is purified by ultrafiltration, isoelectric precipitation and reverse phase chromatography.

3. The process of claim 1, wherein X in SEQ. ID. NO:1 is alanine.

* * * * *